US00PP21333P2

(12) United States Plant Patent
Morrow

(10) Patent No.: US PP21,333 P2
(45) Date of Patent: Sep. 28, 2010

(54) ***GERANIUM* PLANT NAMED 'SYLVIA'S SURPRISE'**

(50) Latin Name: *Geranium wallichianum*
Varietal Denomination: Sylvia's Surprise

(76) Inventor: Sylvia Morrow, 57 Wyndham Drive, CEFN-Y-BEDD, Wrexham CLWD LL12 9YB (GB)

( * ) Notice: Subject to any disclaimer, the term of this patent is extended or adjusted under 35 U.S.C. 154(b) by 0 days.

(21) Appl. No.: 12/319,418

(22) Filed: Jan. 7, 2009

(51) Int. Cl.
*A01H 5/00* (2006.01)

(52) U.S. Cl. ..... Plt./324

(58) Field of Classification Search ..... Plt./324
See application file for complete search history.

*Primary Examiner*—June Hwu
(74) *Attorney, Agent, or Firm*—C. A. Whealy

(57) ABSTRACT

A new and distinct cultivar of *Geranium* plant named 'Sylvia's Surprise', characterized by its upright and outwardly spreading plant habit; vigorous growth habit; freely and continuous flowering habit; pink-colored flowers; long flowering period; and good garden performance.

1 Drawing Sheet

Botanical designation: *Geranium wallichianum.*
Cultivar denomination: 'SYLVIA'S SURPRISE'.

BACKGROUND OF THE INVENTION

The present invention relates to a new and distinct cultivar of *Geranium* plant, botanically known as *Geranium wallichianum,* and hereinafter referred to by the name 'Sylvia's Surprise'.

The new *Geranium* plant is a naturally-occurring whole plant mutation of *Geranium wallichianum* 'Buxton's Variety', not patented. The new *Geranium* was discovered and selected by the Inventor as a single flowering plant from within a population of plants of 'Buxton's Variety' in a controlled outdoor nursery environment in Wrexham, United Kingdom in August, 1999.

Asexual reproduction of the new *Geranium* plant by tissue culture in a controlled environment in Bressingham, United Kingdom since August, 1999, has shown that the unique features of this new *Geranium* plant are stable and reproduced true to type in successive generations.

SUMMARY OF THE INVENTION

Plants of the new *Geranium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sylvia's Surprise'. These characteristics in combination distinguish 'Sylvia's Surprise' as a new and distinct cultivar of *Geranium:*

1. Upright and outwardly spreading plant habit.
2. Vigorous growth habit.
3. Freely and continuous flowering habit.
4. Pink-colored flowers.
5. Long flowering period.
6. Good garden performance.

Plants of the new *Geranium* differ primarily from plants of the parent, 'Buxton's Variety', in flower color as plants of 'Buxton's Variety' have light blue-colored flowers. In addition, plants of the new *Geranium* are more freely flowering than plants of 'Buxton's Variety'.

Plants of the new *Geranium* can be compared to plants of *Geranium* 'Rozanne', disclosed in U.S. Plant Pat. No. 12,175. In side-by-side comparisons conducted in Bressingham, United Kingdom, plants of the new *Geranium* differed primarily from plants of 'Rozanne' in flower color as plants of 'Rozanne' had violet blue-colored flowers with white-colored centers.

BRIEF DESCRIPTION OF THE PHOTOGRAPHS

The accompanying colored photograph illustrates the overall appearance of the new *Geranium*, showing the colors as true as it is reasonably possible to obtain in colored reproductions of this type. Colors in the photographs may differ slightly from the color values cited in the detailed botanical description which accurately describe the colors of the new *Geranium.*

The photograph comprises a side perspective view of a typical flowering plant of 'Sylvia's Surprise'.

DETAILED BOTANICAL DESCRIPTION

The aforementioned photograph and following observations, measurements and values describe plants grown in Bressingham, United Kingdom in an outdoor nursery. During the production of the plants, day temperatures ranged from −1° C. to 28° C. and night temperatures ranged from −5° C. to 15° C. Plants had been growing for 18 months when the photograph and the description were taken. In the detailed description, color references are made to The Royal Horticultural Society Colour Chart, 2001 Edition, except where general terms of ordinary dictionary significance are used.

Botanical classification: *Geranium wallichianum* 'Sylvia's Surprise'.

Parentage: Naturally-occurring whole plant mutation of *Geranium wallichianum* 'Buxton's Variety', not patented.

Propagation:

*Type.*—By tissue culture.

*Time to initiate roots.*—About 15 days at 25° C.

*Time to produce a rooted young plant.*—About 45 days at 25° C.

*Root description.*—Medium to thick in thickness, fleshy; yellowish white in color.

*Rooting habit.*—Moderate branching; moderately dense.

Plant description:

*Plant and growth habit.*—Hardy herbaceous perennial; upright and outwardly spreading plant habit; vigorous growth habit.

*Plant height.*—About 50 cm.

*Plant width.*—About 100 cm.

Foliage description:

*Arrangement.*—Opposite, simple.

*Length.*—About 7 cm.

*Width.*—About 5 cm.

*Shape.*—Deeply dissected.

*Apex.*—Acute.

*Base.*—Sagittate.

*Margin.*—Palmately cleft; lobes biserrate.

*Venation pattern.*—Palmate.

*Texture, upper and lower surfaces.*—Pubescent.

*Color.*—Developing leaves, upper surface: Close to 146B. Developing leaves, lower surface: Close to 146C. Fully developed leaves, upper surface: Close to 137A. Fully developed leaves, lower surface: Close to 137B.

*Petiole.*—Length: About 6 cm. Diameter: About 2 mm. Texture, upper and lower surfaces: Pubescent. Color, upper and lower surfaces: Close to 145A; during the late summer, color is flushed with close to 46B.

Flower description:

*Flowering habit.*—Single campanulate rotate flowers arranged in axillary dichasial cymes; freely flowering habit.

*Fragrance.*—None detected.

*Flowering season.*—In Bressingham, United Kingdom, flowering is continuous from mid-June until first frost; flowers not persistent.

*Flower diameter.*—About 4 cm.

*Flower height.*—About 2 cm.

*Petals.*—Quantity per flower: Five in a single whorl. Length: About 2 cm. Width: About 2.3 cm. Shape: Cordate. Apex: Obtuse. Base: Attenuate. Margin: Entire. Texture, upper and lower surfaces: Smooth, glabrous. Color: When opening and fully opened, upper surface: Close to 68C slightly flushed with close to 91C; center, close to 155D; venation, close to 70B. When opening and fully opened, lower surface: Close to 68D slightly flushed with close to 91D.

*Sepals.*—Quantity per flower: Five, arranged in a single whorl. Length: About 1 cm. Diameter: About 5 mm. Shape: Lanceolate. Apex: Acute. Margin: Entire. Color, upper surface: Close to 138B. Color, lower surface: Close to 138C.

*Peduncles.*—Length: About 4 cm to 8 cm. Diameter: About 2 mm. Color: Close to 145A; during the late summer, color is flushed with close to 46B.

*Reproductive organs.*—Androecium: Stamen quantity per flower: About ten. Anther length: About 3 mm. Anther shape: Oblong. Anther color: Close to 79A. Pollen amount: Scarce. Pollen color: Close to 196D. Gynoecium: Pistil quantity per flower: One. Pistil length: About 1 cm. Pistil color: Close to 79A. Stigma color: Close to 79B. Style color: Close to 79B. Ovary color: Close to 145C.

*Seed/fruits.*—Seed and fruit development have not been observed.

Disease/pest resistance: Plants of the new *Geranium* have not been observed to resistant to pathogens and pests common to *Geraniums*.

Garden performance: Plants of the new *Geranium* have exhibited good garden performance and to tolerate rain and wind and have been observed to be suitable for USDA Zones 5 to 8 and AHS Heat Zones 2 to 12.

It is claimed:

1. A new and distinct *Geranium* plant named 'Sylvia's Surprise' as illustrated and described.

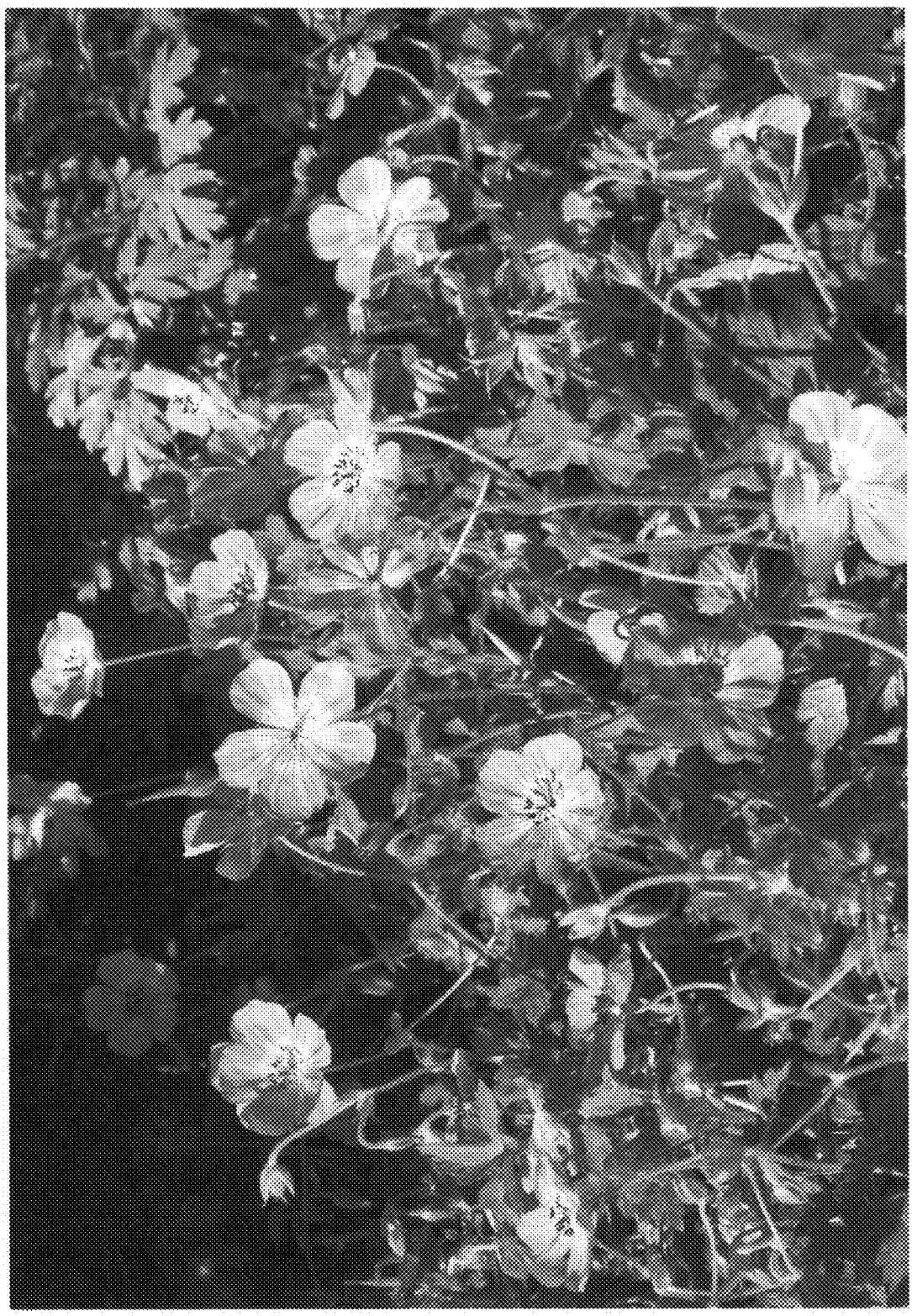

* * * * *